US 12,152,062 B2

(12) United States Patent
Lokireddy et al.

(10) Patent No.: US 12,152,062 B2
(45) Date of Patent: *Nov. 26, 2024

(54) METHOD FOR CONTINUOUS PRODUCTION OF RECOMBINANT GLP-1 PEPTIDE BY BACTERIA

(71) Applicant: ONCOSIMIS BIOTECH PRIVATE LIMITED, Hyderabad (IN)

(72) Inventors: Sudarsanareddy Lokireddy, Hyderabad (IN); Venkata Sri Krishna Kona, Hyderabad (IN)

(73) Assignee: ONCOSIMIS BIOTECH PRIVATED LIMITED, Hyderabad (IN)

( * ) Notice: Subject to any disclaimer, the term of this patent is extended or adjusted under 35 U.S.C. 154(b) by 538 days.

This patent is subject to a terminal disclaimer.

(21) Appl. No.: 17/429,493

(22) PCT Filed: Feb. 24, 2020

(86) PCT No.: PCT/IB2020/051550
§ 371 (c)(1),
(2) Date: Aug. 9, 2021

(87) PCT Pub. No.: WO2020/170228
PCT Pub. Date: Aug. 27, 2020

(65) Prior Publication Data
US 2022/0127324 A1 Apr. 28, 2022

(30) Foreign Application Priority Data
Feb. 24, 2019 (IN) .............................. 201941007166

(51) Int. Cl.
| | | |
|---|---|---|
| C07K 14/605 | (2006.01) | |
| C12M 1/00 | (2006.01) | |
| C12N 15/70 | (2006.01) | |
| C12P 21/00 | (2006.01) | |

(52) U.S. Cl.
CPC ............ *C07K 14/605* (2013.01); *C12N 15/70* (2013.01); *C12P 21/005* (2013.01); *C07K 2319/02* (2013.01)

(58) Field of Classification Search
None
See application file for complete search history.

(56) References Cited

FOREIGN PATENT DOCUMENTS

EP 1408050 B1 4/2004

*Primary Examiner* — Suzanne M Noakes
*Assistant Examiner* — Ciara A McKnight

(57) ABSTRACT

The invention relates to a method for continuously producing and secreting recombinant Glucagon-like peptide-1 (GLP-1) by bacteria, more specifically *E. coli*. More specifically, the invention relates to use of novel bacterial expression vector for producing and enabling extracellular secretion of GLP-1, use of novel media composition for enhancing the secretion and enabling purification, and a perfusion-based fermentation system for continuous production and separation of recombinant GLP-1 peptide.

3 Claims, 6 Drawing Sheets

Specification includes a Sequence Listing.

SEQUENCE LISTING

```
<160> NUMBER OF SEQ ID NOS: 6

<210> SEQ ID NO 1
<211> LENGTH: 93
<212> TYPE: DNA
<213> ORGANISM: Homo sapiens

<400> SEQUENCE: 1
cacgcggaag gcaccttcac cagcgatgtg agcagctacc tggagggtca ggcggcgaaa      60
gaatttatcg cgtggctggt tcgtggtcgt ggc                                  93

<210> SEQ ID NO 2
<211> LENGTH: 99
<212> TYPE: DNA
<213> ORGANISM: Escherichia coli

<400> SEQUENCE: 2
gcgaacaacg aaaccagcaa gagcgtgacc tttccgaaat gcgaagatct ggatgcggcg      60
ggtattgcgg cgagcgttaa gcgtgactac cagcaaaac                            99

<210> SEQ ID NO 3
<211> LENGTH: 99
<212> TYPE: DNA
<213> ORGANISM: Escherichia coli

<400> SEQUENCE: 3
gcgaataatg agaccagcaa aagcgtgacc tttccgaagg cggaggacct ggatgcggcg      60
ggtattgcgg cgagcgttaa acgtgactac cagcaaaac                            99

<210> SEQ ID NO 4
<211> LENGTH: 33
<212> TYPE: PRT
<213> ORGANISM: Escherichia coli

<400> SEQUENCE: 4

Ala Asn Asn Glu Thr Ser Lys Ser Val Thr Phe Pro Lys Cys Glu Asp
1               5                   10                  15
```

```
Leu Asp Ala Ala Gly Ile Ala Ala Ser Val Lys Arg Asp Tyr Gln Gln
            20                  25                  30

Asn

<210> SEQ ID NO 5
<211> LENGTH: 33
<212> TYPE: PRT
<213> ORGANISM: Escherichia coli

<400> SEQUENCE: 5

Ala Asn Asn Glu Thr Ser Lys Ser Val Thr Phe Pro Lys Ala Glu Asp
1               5                   10                  15

Leu Asp Ala Ala Gly Ile Ala Ala Ser Val Lys Arg Asp Tyr Gln Gln
            20                  25                  30

Asn

<210> SEQ ID NO 6
<211> LENGTH: 6793
<212> TYPE: DNA
<213> ORGANISM: Artificial Sequence
<220> FEATURE:
<223> OTHER INFORMATION: Bacterial Expression vector encoding
      recombinant GLP-1 peptide in conjugation with secretory sequence

<400> SEQUENCE: 6
```

| | | | | | |
|---|---|---|---|---|---|
| tggcgaatgg | gacgcgccct | gtagcggcgc | attaagcgcg | gcgggtgtgg | tggttacgcg     60 |
| cagcgtgacc | gctacacttg | ccagcgccct | agcgcccgct | cctttcgctt | tcttcccttc    120 |
| ctttctcgcc | acgttcgccg | gctttccccg | tcaagctcta | aatcggggc | tcccttagg    180 |
| gttccgattt | agtgctttac | ggcacctcga | ccccaaaaaa | cttgattagg | gtgatggttc    240 |
| acgtagtggg | ccatcgccct | gatagacggt | ttttcgccct | ttgacgttgg | agtccacgtt    300 |
| ctttaatagt | ggactcttgt | tccaaactgg | aacaacactc | aaccctatct | cggtctattc    360 |
| ttttgattta | taagggattt | tgccgatttc | ggcctattgg | ttaaaaaatg | agctgattta    420 |
| acaaaaattt | aacgcgaatt | ttaacaaaat | attaacgttt | acaatttcag | gtggcacttt    480 |
| tcggggaaat | gtgcgcggaa | cccctatttg | tttatttttc | taaatacatt | caaatatgta    540 |
| tccgctcatg | aattaattct | tagaaaaact | catcgagcat | caaatgaaac | tgcaatttat    600 |
| tcatatcagg | attatcaata | ccatattttt | gaaaaagccg | tttctgtaat | gaaggagaaa    660 |
| actcaccgag | gcagttccat | aggatggcaa | gatcctggta | tcggtctgcg | attccgactc    720 |
| gtccaacatc | aatacaacct | attaatttcc | cctcgtcaaa | aataaggtta | tcaagtgaga    780 |
| aatcaccatg | agtgacgact | gaatccggtg | agaatggcaa | aagtttatgc | atttctttcc    840 |
| agacttgttc | aacaggccag | ccattacgct | cgtcatcaaa | atcactcgca | tcaaccaaac    900 |
| cgttattcat | tcgtgattgc | gcctgagcga | gacgaaatac | gcgatcgctg | ttaaaaggac    960 |
| aattacaaac | aggaatcgaa | tgcaaccggc | gcaggaacac | tgccagcgca | tcaacaatat   1020 |
| tttcacctga | atcaggatat | tcttctaata | cctggaatgc | tgttttcccg | gggatcgcag   1080 |
| tggtgagtaa | ccatgcatca | tcaggagtac | ggataaaatg | cttgatggtc | ggaagaggca   1140 |
| taaattccgt | cagccagttt | agtctgacca | tctcatctgt | aacatcattg | gcaacgctac   1200 |
| ctttgccatg | tttcagaaac | aactctggcg | catcgggctt | cccatacaat | cgatagattg   1260 |
| tcgcacctga | ttgcccgaca | ttatcgcgag | cccatttata | cccatataaa | tcagcatcca   1320 |
| tgttggaatt | taatcgcggc | ctagagcaag | acgtttcccg | ttgaatatgg | ctcataacac   1380 |
| cccttgtatt | actgtttatg | taagcagaca | gttttattgt | tcatgaccaa | aatcccttaa   1440 |

```
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac accgctgac  gcgcctgac  gggcttgtct   2460 gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataagaaga cagtcataag tgcggcgacg atagtcatgc cccgcgccca    3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
```

```
atcccactac cgagatatcc gcaccaacgc gcagcccgga ctcggtaatg gcgcgcattg      3840
cgcccagcgc catctgatcg ttggcaacca gcatcgcagt gggaacgatg ccctcattca      3900
gcatttgcat ggtttgttga aaaccggaca tggcactcca gtcgccttcc cgttccgcta      3960
tcggctgaat ttgattgcga gtgagatatt tatgccagcc agccgacgcg agacgcgccg      4020
agacagaact taatgggccc gctaacagcg cgatttgctg gtgacccaat gcgaccagat      4080
gctccacgcc cagtcgcgta ccgtcttcat gggagaaaat aatactgttg atgggtgtct      4140
ggtcagagac atcaagaaat aacgccggaa cattagtgca ggcagcttcc acagcaatgg      4200
catcctggtc atccagcgga tagttaatga tcagcccact gacgcgttgc gcgagaagat      4260
tgtgcaccgc cgctttacag gcttcgacgc cgcttcgttc taccatcgac accaccacgc      4320
tggcacccag ttgatcggcg cgagatttaa tcgccgcgac aatttgcgac ggcgcgtgca      4380
gggccagact ggaggtggca acgccaatca gcaacgactg tttgcccgcc agttgttgtg      4440
ccacgcggtt gggaatgtaa ttcagctccg ccatcgccgc ttccactttt tcccgcgttt      4500
tcgcagaaac gtggctggcc tggttcacca cgcgggaaac ggtctgataa gagacaccgg      4560
catactctgc gacatcgtat aacgttactg gtttcacatt caccaccctg aattgactct      4620
cttccgggcg ctatcatgcc ataccgcgaa aggttttgcg ccattcgatg gtgtccggga      4680
tctcgacgct ctcccttatg cgactcctgc attaggaagc agcccagtag taggttgagg      4740
ccgttgagca ccgccgccgc aaggaatggt gcatgcaagg agatggcgcc caacagtccc      4800
ccggccacgg ggcctgccac catacccacg ccgaaacaag cgctcatgag cccgaagtgg      4860
cgagcccgat cttcccccatc ggtgatgtcg gcgatatagg cgccagcaac cgcacctgtg      4920
gcgccggtga tgccggccac gatgcgtccg gcgtagagga tcgagatcta cgaaacgg      4980 gaatgcggta attacgcttt gttttttataa gtcagatttt aattttttatt ggttaacata      5040 acgaaaggta aaatacataa ggcttactaa aagccagata acagtatgcg tatttgcgcg      5100
ctgatttttg cggtataaga atatatactg atatgtatac ccgaagtatg tcaaaaagag      5160
gtgtgctatg aagcagcgta ttacagtgac agttgacagc gacagctatc agttgctcaa      5220
ggcatatgat gtcaatatct ccggtctggt aagcacaacc atgcagaatg aagcccgtcg      5280
tctgcgtgcc gaacgctgga aagcggaaaa tcaggaaggg atggctgagg tcgcccggtt      5340
tattgaaatg aacggctctt ttgctgacga gaacagggac tggtgaaatg cagtttaagg      5400
tttacaccta taaagagag agccgttatc gtctgtttgt ggatgtacag agtgatatta      5460
ttgacacgcc cggcgacgg atggtgatcc ccctggccag tgcacgtctg ctgtcagata      5520
aagtctcccg tgaactttac ccggtggtgc atatcgggga tgaaagctgg cgcatgatga      5580
ccaccgatat ggccagtgtg ccggtctccg ttatcgggga agaagtggct gatctcagcc      5640
accgcgaaaa tgacatcaaa aacgccatta acctgatgtt ctggggaata taaatgtcag      5700
gctccgttat acacagccag tctgcagcga tcccgcgaaa tttgacaatt aatcatcggc      5760
tcgtataatg tgtggaattg tgagcggata acaattcccc tctagaaata attttgttta      5820
actttaagaa ggagatatac atatgatgaa acgtaatatc ctggcggtga ttgttccggc      5880
gctgctggtt gcgggcaccg cgaatgcggc gaataatgag accagcaaaa gcgtgacctt      5940
tccgaaggcg gaggacctgg atgcggcggg tattgcggcg agcgttaaac gtgactacca      6000
gcaaaacggt ggcagcggtg gcagcggtag ccaccatcat catcaccaca gcagcggtgg      6060
cagcggtacc gactataagg acgatgacga taaaacgcg gaaggcacct ttaccagcga      6120
tgtgagcagc tacctggagg gtcaagcggc gaaggagttc attgcgtggc tggtgcgtgg      6180
```

```
tcgtggctaa tagtgagcgg ccgcggctgt tttggcggat gagagaagat tttcagcctg    6240
atacagatta aatcagaacg cagaagcggt ctgataaaac agaatttgcc tggcggcagt    6300
agcgcggtgg tcccacctga ccccatgccg aactcagaag tgaaacgccg tagcgccgat    6360
ggtagtgtgg ggtctcccca tgcgagagta gggaactgcc aggcatcaaa taaaacgaaa    6420
ggctcagtcg aaagactggg cctttcgttt tatctgttgt ttgtcggtga acgctctcct    6480
gagtaggaca aatccgccgg gagcggattt gaacgttgcg aagcaacggc ccggagggtg    6540
gcgggcagga cgcccgccat aaactgccag gcatcaaatt aagcagaagg ccatcctgac    6600
ggatggcctt tttgcgtttc tacaaactct ctcgagcacc accaccacca ccactgagat    6660
ccggctgcta acaaagcccg aaaggaagct gagttggctg ctgccaccgc tgagcaataa    6720
ctagcataac cccttgggc ctctaaacgg gtcttgaggg gttttttgct gaaaggagga    6780
actatatccg gat                                                       6793
```

METHOD FOR CONTINUOUS PRODUCTION OF RECOMBINANT GLP-1 PEPTIDE BY BACTERIA

RELATED APPLICATIONS

This application claims priority from the PCT application No. PCT/IB2020/051550 filed on 24 Feb. 2020, which claims priority to the Indian provisional patent application numbered 201941007166 titled "Method for continuous production of recombinant glp-1 peptide by bacteria" filed on 24 Feb. 2019. Both applications are incorporated in full herein by reference.

FIELD OF THE INVENTION

The invention relates to a method for continuous production and secretion of recombinant Glucagon-like peptide-1 (GLP-1) by bacteria, more specifically, E. coli.

BACKGROUND OF THE INVENTION

Glucagon-like peptide 1 (GLP-1) is a 31 amino acid potent incretin hormone produced in the L-cells of the distal ileum and colon. In the L-cells, GLP-1 is generated by tissue-specific posttranslational processing of the proglucagon gene. Nutrients, including glucose, fatty acids, and dietary fiber, are all known to upregulate the transcription of the gene encoding GLP-1, and they can stimulate the release of this hormone.

The initial product GLP-1 (1-37) is susceptible to amidation and proteolytic cleavage which gives rise to the two truncated and equipotent biologically active forms, GLP-1 (7-36) amide and GLP-1 (7-37).

GLP-1 is an incretin; thus exhibits insulinotropic effects i.e. have the ability to decrease blood sugar levels in a glucose-dependent manner by enhancing the secretion of insulin. Besides the insulinotropic effects, GLP-1 has been associated with numerous regulatory and protective effects. The action of GLP-1 is known in patients with type 2 diabetes and substantial pharmaceutical research has therefore been directed towards the development of GLP-1-based treatment. GLP-1 has also been implicated as a possible therapeutic agent for the management related metabolic disorders, such as obesity.

Hence, owing to the importance of production of GLP-1 there is a technological gap wherein a method for producing of recombinant GLP-1 peptide is required using recombinant bacteria, more specifically E. coli with high rate of production.

OBJECT OF THE INVENTION

The main object of the invention is to provide a method for continuous production and secretion of recombinant GLP-1 peptide by bacteria, more specifically E. coli, wherein, the recombinant GLP-1 is produced in the bacteria by using a novel bacterial expression vector and secreted extracellularly by culturing the bacteria in a chemically defined media using a perfusion-based fermentation system.

Another object of the invention is to provide a method for enhancing secretion of recombinant GLP-1 by using a novel bacterial expression vector comprising of DNA sequence encoding GLP-1 peptide represented by Seq. ID 1; and at least one secretory signal sequence comprising of a DNA sequence; and at least one affinity tag sequence for enabling purification of GLP-1 peptide.

Yet another object of the invention is to provide a method for producing recombinant GLP-1 which is easily purified using chemically defined media.

Yet another object of the invention is to provide a system and method for enhanced production, and secretion of recombinant GLP-1 in bacteria with a customized separation system for alternating tangential filtration flow for continues removal of secreted recombinant GLP-1 from a culturing suspension.

SUMMARY OF THE INVENTION

The present invention relates to method for producing recombinant GLP-1 using bacteria. More specifically, the invention relates to producing and secreting recombinant GLP-1 by E. coli.

In the main embodiment, the invention provides a method for producing GLP-1 in bacteria, more specifically, E. coli, comprising the steps of transforming E. coli with a bacterial expression vector of Seq. ID 6, carrying the DNA sequence encoding GLP-1 represented by Seq. ID 1 in conjugation with at least one secretory signal sequence; preparing a starter culture of recombinant E. coli by growing the culture at 37° C. with 225 rpm for 12 hours in a starter culture growth media till $OD_{600}$ of the starter culture reaches 5.0-6.0; preparing a perfusion-based fermenter system by adding initial batch media to the fermenter vessel comprising of glucose/dextrose at a concentration of 10 g/L and maintaining the pH at 6.9; adding the starter culture to the fermenter vessel and maintaining the pH at 6.9 using 3N NaOH in the first hour and after first hour using 4M liquid ammonia; adding lac operon inducing agent such as lactose or lactose analogs to the fermenter vessel when the residual glucose/dextrose concentration in the initial batch media has reduced to ~5 g/L for induction of production and secretion of recombinant GLP-1 peptide from recombinant E. coli; and initiating perfusion-based fermentation system after 30-40 mins of induction for separating the recombinant E. coli as retentate from the spent culture media containing the secreted recombinant GLP-1 peptide as permeate, harvesting recombinant GLP-1 peptide from the permeate, and re-feeding the fermenter vessel with fresh perfusion media and with the retentate recombinant E. coli for continuous production and secretion of recombinant GLP-1 peptide.

In yet another embodiment, the recombinant expression vector using Seq. ID 6 secretes the recombinant GLP-1 peptide in the range of 1-1.2 g/L/hr using perfusion-based fermentation system.

In another embodiment the invention provides the starter culture media, the initial batch media, and the perfusion media which are chemically defined media having the composition as described in Table 2.

In yet another embodiment, the invention provides a perfusion-based fermentation system enabling culture medium including the recombinant E. coli to be circulated over a separation system in alternating tangential flow, and the separation system removes a filtrate containing spent medium containing recombinant GLP-1 peptide from the culture medium and retains the recombinant E. coli in the culture medium for continuous production.

In yet another embodiment, the invention provides a novel bacterial expression vector comprising of:
1) a DNA sequence Seq. ID 1 encoding GLP-1 peptide;
2) at least one secretory signal sequence which is a combination of a) at least one DNA sequence encoding a signal sequence of genes selected from the group consisting of pelB, ompA, yebF, and ompF, and b) at least one DNA sequence encoding a carrier peptide, preferably, DNA sequence Seq. ID 2 or Seq. ID 3, encoding truncated yebF of Seq. ID 4 or Seq. ID 5 respectively;
3) at least one gene expression cassette comprising of at least one inducible promoter, an RBS, DNA sequence encoding the recombinant GLP-1 peptide, DNA sequence encoding an affinity tag, and at least one gene terminator; with the secretory signal sequence, and the DNA sequence of the affinity tag operably linked to the DNA sequence of the recombinant GLP-1 peptide;

4) at least one bacterial on gene sequence for replication of the vector in the host bacterial cell; and
5) at least one DNA sequence for coding a selectable marker with a suitable promoter and a gene terminator sequence flanking the DNA sequence of the selectable marker.

The invention further provides a DNA sequence encoding recombinant GLP-1 Seq. ID 1.

The invention also provides an expression vector Seq. ID 6 for production and secretion of recombinant GLP-1 peptide in E. coli.

The invention also relates to perfusion-based fermenter system, wherein, the system provides a feed tank; a feed pump; a level sensor, a motor; a fermenter vessel; a magnetic levitation pump, separation module, harvest pump, and a harvest tank, wherein hallow fiber column in the separation module comprises a filter module comprising a filter module of hollow fiber membranes suitable for the removal of secreted recombinant protein from the culture medium. The separation module comprises a filter module comprising hollow fibers, e.g. hollow fibers made of polysulphone, Methyl Ester or Cellulose ester having a porosity of between 0.4 µm and 0.1 µm, e.g. a porosity of 0.2 µm. The separation system further comprises a filter module comprising membranes wherein the membranes have a molecular weight cut-off pore size of 500 kDa.

BRIEF DESCRIPTION OF DRAWING(S)

A complete understanding of the system and method of the present invention is obtained by reference to the following figure(s):

FIG. 1 is a schematic representation of a bacterial expression vector for encoding and secreting recombinant GLP-1 peptide from E. coli;

FIG. 2 elucidates the schematic diagram of the perfusion-based fermentation system;

Figure 5:
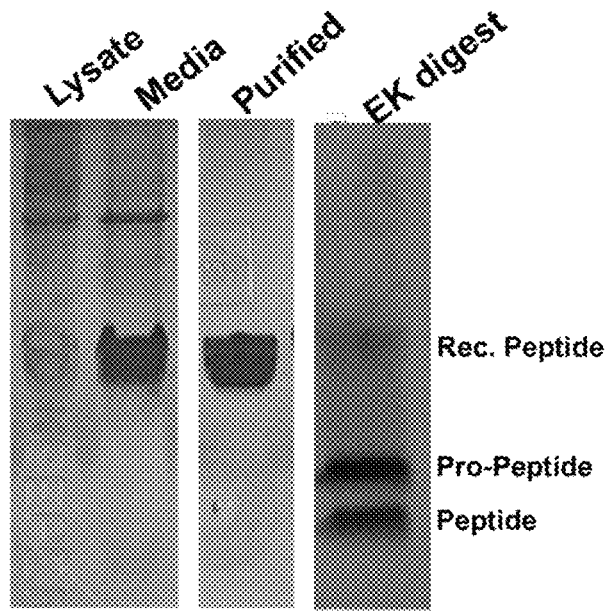
Figure 6A:
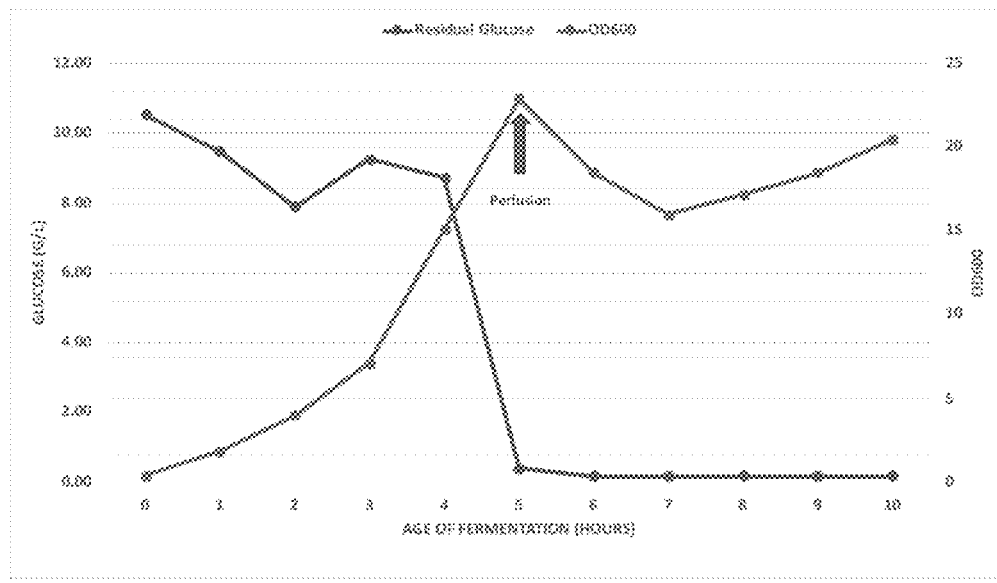
Figure 6B:
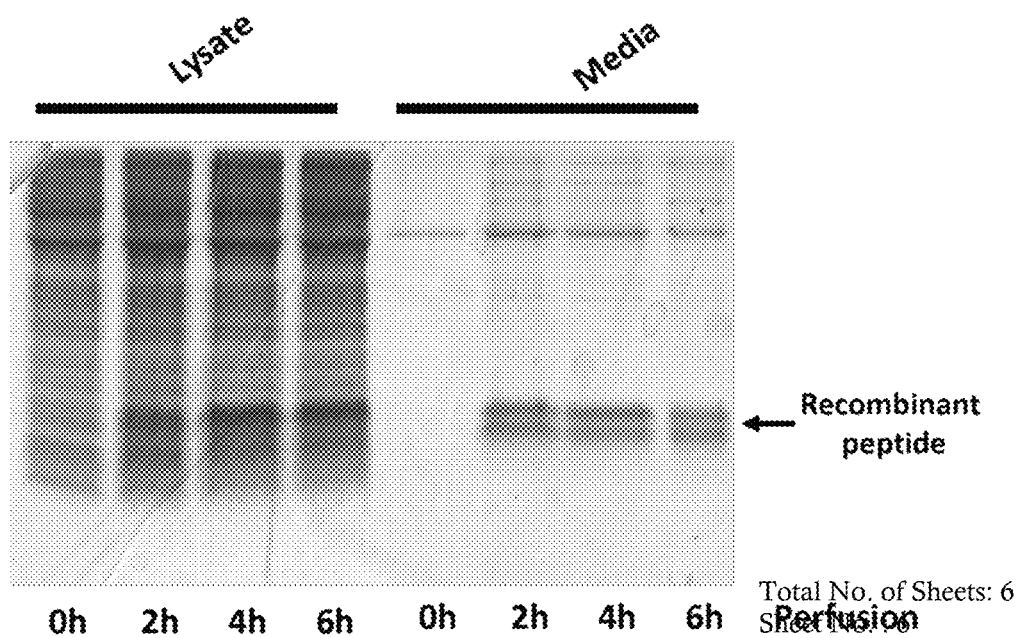
Figure 6C:
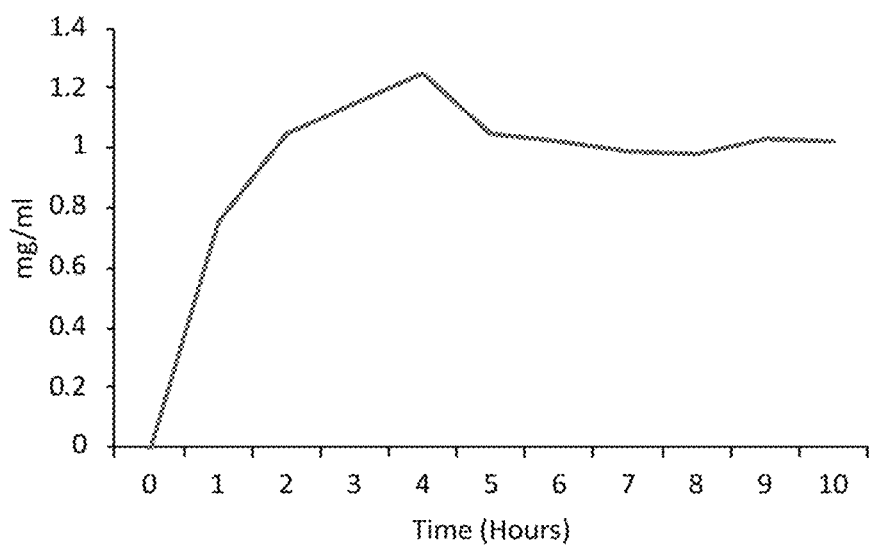

FIG. 5 is representative image of SDS-PAGE for recombinant GLP-1 peptide in recombinant E. coli transformed with expression vector Seq. ID 6 and media of batch fermentation process; His-purified recombinant GLP-1 peptide; and enterokinase digested recombinant GLP-1 peptide;

FIG. 6a is a graphical representation of growth kinetics of recombinant E. coli transformed with expression vector Seq. ID 6 and glucose consumption over time in perfusion-based fermentation process;

FIG. 6b is representative image of SDS-PAGE analysis of 10 kDa GLP-1 peptide secretion is seen. Media samples were collected and analyzed after 0, 2, 4 and 6 hours of induction with 0.25 mM IPTG; and FIG. 6c is a graphical representation of rate of production recombinant GLP-1 peptide in every hour of perfusion-based fermentation system for a period of 10 hours.

DETAILED DESCRIPTION OF THE INVENTION

Abbreviations Used pelB refers to: leader DNA sequence encoding the N-terminal amino acid residues of pectatelyase B
ompA refers to: leader DNA sequence encoding the amino acid residues of Outer membrane protein A
ompF refers to: leader DNA sequence encoding the amino acid residues of Outer membrane protein F
yebF refers to: leader DNA sequence encoding the amino acid residues of protein yebF
AmpR refers to: DNA sequence encoding ampicillin resistance gene
F1 Ori Origin of replication
IPTG Isopropyl β-d-1-thiogalactopyranoside
Lac or Lac1 DNA sequence encodes lac repressor
RBS Ribosomal binding site The present invention now will be described hereinafter with reference to the detailed description, in which some, but not all embodiments of the invention are indicated. Indeed, the invention may be embodied in many different forms and should not be construed as limited to the embodiments set forth herein; rather, these embodiments are provided so that this disclosure will satisfy applicable legal requirements. Like numbers refer to like elements throughout. The present invention is described fully herein with non-limiting embodiments and exemplary experimentation.

The present invention relates to producing and secreting recombinant GLP-1 peptide by E. coli. More specifically, the invention relates to producing and secreting GLP-1 by E. coli, followed by its separation using a perfusion-based fermentation system.

Figure 1:
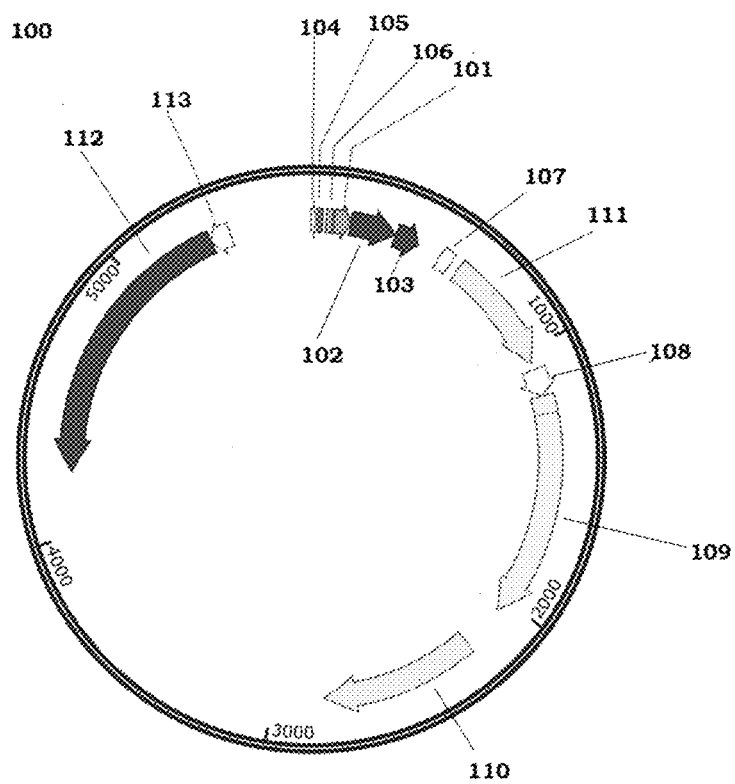

In the main embodiment, as described in FIG. 1, the invention provides a bacterial expression vector 100, particularly for E. coli, for producing and secreting recombinant GLP-1 peptide. The expression vector comprises of DNA sequence encoding GLP-1 peptide 103; and at least one secretory signal sequence which is a combination of a) at least one DNA sequence encoding a signal sequence of genes 101 selected from the group consisting of pelB, ompA, yebF, and ompF, and b) at least one DNA sequence encoding a carrier peptide 102, preferably, DNA sequence Seq. ID 2 or Seq. ID 3, encoding truncated yebF of Seq. ID 4 or Seq. ID 5 respectively. The expression vector further comprises of at least one gene expression cassette operably linked to DNA sequence encoding GLP-1 peptide 103 comprising of at least one inducible promoter 104, an RBS 105, DNA sequence of an affinity tag, and at least one gene terminator 106. The secretory signal sequence 101 and 102, and the DNA sequence of the affinity tag are operably linked to the DNA sequence of the recombinant GLP-1 peptide 103. Further the expression vector comprises of at least one bacterial on gene sequence 110 for replication of the vector in the host bacterial cell; and at least one antibiotic resistance gene 109 and at least one additional selection marker 112 each controlled by their respective gene promoters 108, and 113. The expression vector additionally comprises of at least one f1 on sequence 111 for enabling packaging of recombinant GLP-1 peptide in F1 bacteriophage system.

The affinity tag sequence is for enabling purification of recombinant GLP-1 peptide.

Further, the DNA sequence encoding recombinant GLP-1 peptide is separated from the secretory signal sequence by Enterokinase recognition sequence (DDDDK) to enable separation of recombinant GLP-1 peptide from the secretory signal sequence after harvesting the recombinant GLP-1 peptide.

The GLP-1 peptide comprises of 7-37 amino acid stretch of human GLP-1 protein (NCBI reference no AAP35459) encoded by Seq. ID 1; and Table 1 provides the DNA and Peptide sequences used in the bacterial expression vector.

TABLE 1 Provide DNA and Peptide Sequences

| Name of peptide | Seq. ID no. and DNA sequence | Seq. ID no. and Peptide sequence |
|---|---|---|
| GLP-1 Peptide | Seq. ID 1<br>CACGCGGAAGGCACCTTCACCAGCGATGTGA<br>GCAGCTACCTGGAGGGTCAGGCGGCGAAAGA<br>ATTTATCGCGTGGCTGGTTCGTGGTCGTGGC | HAEGTFT<br>SDVSSYLE<br>GQAAKEF<br>IAWLVRG<br>RG |
| Signal Sequence | | |
| pelB | ATGAAATACCTGTTACCTACCGCGGCTGCGGG<br>GCTGCTGCTGTTAGCAGCTCAGCCGGCAATGG<br>CT | MKYLLPT<br>AAAGLLL<br>LAAQPAM<br>A |
| yebF | ATGAAAAAGCGTGGTGCGTTCCTGGGCCTGCT<br>GCTGGTTAGCGCGTGCGCGAGCGTGTTTGCG | MKKRGAF<br>LGLLLVS<br>ACASVFA |
| ompA | ATGAAGAAGACCGCGATTGCGATTGCGGTGG<br>CGCTGGCGGGTTTTGCGACCGTGGCGCAGGC<br>G | MKKTAIAI<br>AVALAGF<br>ATVAQA |
| ompF | ATGATGAAGCGCAATATTCTGGCAGTGATCGT<br>CCCTGCTCTGTTAGTAGCAGGTACTGCAAACG<br>CT | MMKRNIL<br>AVIVPALL<br>VAGTANA |
| Carrier peptide | | |
| Truncated yebf peptide | Seq. ID 2<br>GCGAACAACGAAACCAGCAAGAGCGTGACCT<br>TTCCGAAATGCGAAGATCTGGATGCGGCGGG<br>TATTGCGGCGAGCGTTAAGCGTGACTACCAGC<br>AAAAC | Seq. ID 4<br>ANNETSK<br>SVTFPKCE<br>DLDAAGI<br>AASVKRD<br>YQQN |
| Truncated yebf peptide | Seq. ID 3<br>GCGAATAATGAGACCAGCAAAAGCGTGACCT<br>TTCCGAAGGCGGAGGACCTGGATGCGGCGGG<br>TATTGCGGCGAGCGTTAAACGTGACTACCAGC<br>AAAAC | Seq. ID 5<br>ANNETSK<br>SVTFPKAE<br>DLDAAGI<br>AASVKRD<br>YQQN |
| Expression vector | Seq. ID 6<br>TGGCGAATGGGACGCGCCCTGTAGCGGCGCATTAAGCGCG<br>GCGGGTGTGGTGGTTACGCGCAGCGTGACCGCTACACTTG<br>CCAGCGCCCTAGCGCCCGCTCCTTTCGCTTTCTTCCCTTCCT<br>TTCTCGCCACGTTCGCCGGCTTTCCCCGTCAAGCTCTAAATC<br>GGGGGCTCCCTTTAGGGTTCCGATTTAGTGCTTTACGGCAC<br>CTCGACCCCAAAAAACTTGATTAGGGTGATGGTTCACGTAG<br>TGGGCCATCGCCCTGATAGACGGTTTTTCGCCCTTTGACGT<br>TGGAGTCCACGTTCTTTAATAGTGGACTCTTGTTCCAAACT<br>GGAACAACACTCAACCCTATCTCGGTCTATTCTTTTGATTTA<br>TAAGGGATTTTGCCGATTTCGGCCTATTGGTTAAAAAATGA<br>GCTGATTTAACAAAAATTTAACGCGAATTTTAACAAAATAT<br>TAACGTTTACAATTTCAGGTGGCACTTTTCGGGGAAATGTG<br>CGCGGAACCCCTATTTGTTTATTTTTCTAAATACATTCAAAT<br>ATGTATCCGCTCATGAATTAATTCTTAGAAAAACTCATCGA<br>GCATCAAATGAAACTGCAATTTATTCATATCAGGATTATCA<br>ATACCATATTTTTGAAAAAGCCGTTTCTGTAATGAAGGAGA<br>AAACTCACCGAGGCAGTTCCATAGGATGGCAAGATCCTGG<br>TATCGGTCTGCGATTCCGACTCGTCCAACATCAATACAACC<br>TATTAATTTCCCCTCGTCAAAAATAAGGTTATCAAGTGAGA<br>AATCACCATGAGTGACGACTGAATCCGGTGAGAATGGCAA<br>AAGTTTATGCATTTCTTTCCAGACTTGTTCAACAGGCCAGCC<br>ATTACGCTCGTCATCAAAATCACTCGCATCAACCAAACCGT<br>TATTCATTCGTGATTGCGCCTGAGCGAGACGAAATACGCGA<br>TCGCTGTTAAAAGGACAATTACAAACAGGAATCGAATGCA<br>ACCGGCGCAGGAACACTGCCAGCGCATCAACAATATTTTCA<br>CCTGAATCAGGATATTCTTCTAATACCTGGAATGCTGTTTTC<br>CCGGGGATCGCAGTGGTGAGTAACCATGCATCATCAGGAG<br>TACGGATAAAATGCTTGATGGTCGGAAGAGGCATAAATTC<br>CGTCAGCCAGTTTAGTCTGACCATCTCATCTGTAACATCATT<br>GGCAACGCTACCTTTGCCATGTTTCAGAAACAACTCTGGCG |

| Name of peptide | Seq. ID no. and DNA sequence | Seq. ID no. and Peptide sequence |
|---|---|---|
| | CATCGGGCTTCCCATACAATCGATAGATTGTCGCACCTGAT | |
| | TGCCCGACATTATCGCGAGCCCATTTATACCCATATAAATC | |
| | AGCATCCATGTTGGAATTTAATCGCGGCCTAGAGCAAGAC | |
| | GTTTCCCGTTGAATATGGCTCATAACACCCCTTGTATTACTG | |
| | TTTATGTAAGCAGACAGTTTTATTGTTCATGACCAAAATCCC | |
| | TTAACGTGAGTTTTCGTTCCACTGAGCGTCAGACCCCGTAG | |
| | AAAAGATCAAAGGATCTTCTTGAGATCCTTTTTTTCTGCGC | |
| | GTAATCTGCTGCTTGCAAACAAAAAAACCACCGCTACCAGC | |
| | GGTGGTTTGTTTGCCGGATCAAGAGCTACCAACTCTTTTTC | |
| | CGAAGGTAACTGGCTTCAGCAGAGCGCAGATACCAAATAC | |
| | TGTCCTTCTAGTGTAGCCGTAGTTAGGCCACCACTTCAAGA | |
| | ACTCTGTAGCACCGCCTACATACCTCGCTCTGCTAATCCTGT | |
| | TACCAGTGGCTGCTGCCAGTGGCGATAAGTCGTGTCTTACC | |
| | GGGTTGGACTCAAGACGATAGTTACCGGATAAGGCGCAGC | |
| | GGTCGGGCTGAACGGGGGGTTCGTGCACACAGCCCAGCTT | |
| | GGAGCGAACGACCTACACCGAACTGAGATACCTACAGCGT | |
| | GAGCTATGAGAAAGCGCCACGCTTCCCGAAGGGAGAAAG | |
| | GCGGACAGGTATCCGGTAAGCGGCAGGGTCGGAACAGGA | |
| | GAGCGCACGAGGGAGCTTCCAGGGGGAAACGCCTGGTATC | |
| | TTTATAGTCCTGTCGGGTTTCGCCACCTCTGACTTGAGCGTC | |
| | GATTTTTGTGATGCTCGTCAGGGGGCGGAGCCTATGGAA | |
| | AAACGCCAGCAACGCGGCCTTTTTACGGTTCCTGGCCTTTT | |
| | GCTGGCCTTTTGCTCACATGTTCTTTCCTGCGTTATCCCCTG | |
| | ATTCTGTGGATAACCGTATTACCGCCTTTGAGTGAGCTGAT | |
| | ACCGCTCGCCGCAGCCGAACGACCGAGCGCAGCGAGTCAG | |
| | TGAGCGAGGAAGCGGAAGAGCGCCTGATGCGGTATTTTCT | |
| | CCTTACGCATCTGTGCGGTATTTCACACCGCATATATGGTG | |
| | CACTCTCAGTACAATCTGCTCTGATGCCGCATAGTTAAGCC | |
| | AGTATACACTCCGCTATCGCTACGTGACTGGGTCATGGCTG | |
| | CGCCCCGACACCCGCCAACACCCGCTGACGCGCCCTGACG | |
| | GGCTTGTCTGCTCCCGGCATCCGCTTACAGACAAGCTGTGA | |
| | CCGTCTCCGGGAGCTGCATGTGTCAGAGGTTTTCACCGTCA | |
| | TCACCGAAACGCGCGAGGCAGCTGCGGTAAAGCTCATCAG | |
| | CGTGGTCGTGAAGCGATTCACAGATGTCTGCCTGTTCATCC | |
| | GCGTCCAGCTCGTTGAGTTTCTCCAGAAGCGTTAATGTCTG | |
| | GCTTCTGATAAAGCGGGCCATGTTAAGGGCGGTTTTTTCCT | |
| | GTTTGGTCACTGATGCCTCCGTGTAAGGGGATTTCTGTTC | |
| | ATGGGGGTAATGATACCGATGAAACGAGAGAGGATGCTCA | |
| | CGATACGGGTTACTGATGATGAACATGCCCGGTTACTGGA | |
| | ACGTTGTGAGGGTAAACAACTGGCGGTATGGATGCGGCGG | |
| | GACCAGAGAAAAATCACTCAGGGTCAATGCCAGCGCTTCG | |
| | TTAATACAGATGTAGGTGTTCCACAGGGTAGCCAGCAGCA | |
| | TCCTGCGATGCAGATCCGGAACATAATGGTGCAGGGCGCT | |
| | GACTTCCGCGTTTCCAGACTTTACGAAACACGGAAACCGAA | |
| | GACCATTCATGTTGTTGCTCAGGTCGCAGACGTTTTGCAGC | |
| | AGCAGTCGCTTCACGTTCGCTCGCGTATCGGTGATTCATTC | |
| | TGCTAACCAGTAAGGCAACCCCGCCAGCCTAGCCGGGTCC | |
| | TCAACGACAGGAGCACGATCATGCGCACCCGTGGGCCGC | |
| | CATGCCGGCGATAATGGCCTGCTTCTCGCCGAAACGTTTGG | |
| | TGGCGGGACCAGTGACGAAGGCTTGAGCGAGGGCGTGCA | |
| | AGATTCCGAATACCGCAAGCGACAGGCCGATCATCGTCGC | |
| | GCTCCAGCGAAAGCGGTCCTCGCCGAAAATGACCCAGAGC | |
| | GCTGCCGGCACCTGTCCTACGAGTTGCATGATAAAGAAGA | |
| | CAGTCATAAGTGCGGCGACGATAGTCATGCCCCGCGCCCA | |
| | CCGGAAGGAGCTGACTGGGTTGAAGGCTCTCAAGGGCATC | |
| | GGTCGAGATCCCGGTGCCTAATGAGTGAGCTAACTTACATT | |
| | AATTGCGTTGCGCTCACTGCCCGCTTTCCAGTCGGGAAACC | |
| | TGTCGTGCCAGCTGCATTAATGAATCGGCCAACGCGCGGG | |
| | GAGAGGCGGTTTGCGTATTGGGCGCCAGGGTGGTTTTTCTT | |
| | TTCACCAGTGAGACGGGCAACAGCTGATTGCCCTTCACCGC | |
| | CTGGCCCTGAGAGAGTTGCAGCAAGCGGTCCACGCTGGTT | |
| | TGCCCCAGCAGGCGAAAATCCTGTTTGATGGTGGTTAACG | |
| | GCGGGATATAACATGAGCTGTCTTCGGTATCGTCGTATCCC | |
| | ACTACCGAGATATCCGCACCAACGCGCAGCCCGGACTCGG | |
| | TAATGGCGCGCATTGCGCCCAGCGCCATCTGATCGTTGGCA | |
| | ACCAGCATCGCAGTGGGAACGATGCCCTCATTCAGCATTTG | |
| | CATGGTTTGTTGAAAACCGGACATGGCACTCCAGTCGCCTT | |
| | CCCGTTCCGCTATCGGCTGAATTTGATTGCGAGTGAGATAT | |
| | TTATGCCAGCCAGCCAGACGCAGACGCGCCGAGACAGAAC | |
| | TTAATGGGCCCGCTAACAGCGCGATTTGCTGGTGACCCAAT | |
| | GCGACCAGATGCTCCACGCCCAGTCGCGTACCGTCTTCATG | |
| | GGAGAAAATAATACTGTTGATGGGTGTCTGGTCAGAGACA | |
| | TCAAGAAATAACGCCGGAACATTAGTGCAGGCAGCTTCCA | |
| | CAGCAATGGCATCCTGGTCATCCAGCGGATAGTTAATGATC | |
| | AGCCCACTGACGCGTTGCGCGAGAAGATTGTGCACCGCCG | |

| Name of peptide | Seq. ID no. and DNA sequence | Seq. ID no. and Peptide sequence |
|---|---|---|
| | CTTTACAGGCTTCGACGCCGCTTCGTTCTACCATCGACACC | |
| | ACCACGCTGGCACCCAGTTGATCGGCGCGAGATTTAATCGC | |
| | CGCGACAATTTGCGACGGCGCGTGCAGGGCCAGACTGGAG | |
| | GTGGCAACGCCAATCAGCAACGACTGTTTGCCCGCCAGTTG | |
| | TTGTGCCACGCGGTTGGGAATGTAATTCAGCTCCGCCATCG | |
| | CCGCTTCCACTTTTTCCCGCGTTTTCGCAGAAACGTGGCTG | |
| | GCCTGGTTCACCACGCGGGAAACGGTCTGATAAGAGACAC | |
| | CGGCATACTCTGCGACATCGTATAACGTTACTGGTTTCACA | |
| | TTCACCACCCTGAATTGACTCTCTTCCGGGCGCTATCATGCC | |
| | ATACCGCGAAAGGTTTTGCGCCATTCGATGGTGTCCGGGAT | |
| | CTCGACGCTCTCCCTTATGCGACTCCTGCATTAGGAAGCAG | |
| | CCCAGTAGTAGGTTGAGGCCGTTGAGCACCGCCGCCGCAA | |
| | GGAATGGTGCATGCAAGGAGATGGCGCCCAACAGTCCCCC | |
| | GGCCACGGGGCCTGCCACCATACCCACGCCGAAACAAGCG | |
| | CTCATGAGCCCGAAGTGGCGAGCCCGATCTTCCCCATCGGT | |
| | GATGTCGGCGATATAGGCGCCAGCAACCGCACCTGTGGCG | |
| | CCGGTGATGCCGGCCACGATGCGTCCGGCGTAGAGGATCG | |
| | AGATCTATACGAAACGGGAATGCGGTAATTACGCTTTGTTT | |
| | TTATAAGTCAGATTTTAATTTTTATTGGTTAACATAACGAAA | |
| | GGTAAAATACATAAGGCTTACTAAAAGCCAGATAACAGTA | |
| | TGCGTATTTGCGCGCTGATTTTTGCGGTATAAGAATATATA | |
| | CTGATATGTATACCCGAAGTATGTCAAAAAGAGGTGTGCTA | |
| | TGAAGCAGCGTATTACAGTGACAGTTGACAGCGACAGCTA | |
| | TCAGTTGCTCAAGGCATATGATGTCAATATCTCCGGTCTGG | |
| | TAAGCACAACCATGCAGAATGAAGCCCGTCGTCTGCGTGC | |
| | CGAACGCTGGAAAGCGGAAAATCAGGAAGGGATGGCTGA | |
| | GGTCGCCCGGTTTATTGAAATGAACGGCTCTTTTGCTGACG | |
| | AGAACAGGGACTGGTGAAATGCAGTTTAAGGTTTACACCT | |
| | ATAAAAGAGAGAGCCGTTATCGTCTGTTTGTGGATGTACA | |
| | GAGTGATATTATTGACACGCCCGGGCGACGGATGGTGATC | |
| | CCCCTGGCCAGTGCACGTCTGCTGTCAGATAAAGTCTCCCG | |
| | TGAACTTTACCCGGTGGTGCATATCGGGGATGAAAGCTGG | |
| | CGCATGATGACCACCGATATGGCCAGTGTGCCGGTCTCCGT | |
| | TATCGGGGAAGAAGTGGCTGATCTCAGCCACCGCGAAAAT | |
| | GACATCAAAAACGCCATTAACCTGATGTTCTGGGGAATATA | |
| | AATGTCAGGCTCCGTTATACACAGCCAGTCTGCAGCGATCC | |
| | CGCGAAATTTGACAATTAATCATCGGCTCGTATAATGTGTG | |
| | GAATTGTGAGCGGATAACAATTCCCCTCTAGAAATAATTTT | |
| | GTTTAACTTTAAGAAGGAGATATACATATGATGAAACGTAA | |
| | TATCCTGGCGGTGATTGTTCCGGCGCTGCTGGTTGCGGGCA | |
| | CCGCGAATGCGGCGAATAATGAGACCAGCAAAAGCGTGAC | |
| | CTTTCCGAAGGCGGAGGACCTGGATGCGGCGGGTATTGCG | |
| | GCGAGCGTTAAACGTGACTACCAGCAAAACGGTGGCAGCG | |
| | GTGGCAGCGGTAGCCACCATCATCATCACCACAGCAGCGG | |
| | TGGCAGCGGTACCGACTATAAGGACGATGACGATAAACAC | |
| | GCGGAAGGCACCTTTACCAGCGATGTGAGCAGCTACCTGG | |
| | AGGGTCAAGCGGCGAAGGAGTTCATTGCGTGGCTGGTGCG | |
| | TGGTCGTGGCTAATAGTGAGCGGCCGCGGCTGTTTTGGCG | |
| | GATGAGAGAAGATTTTCAGCCTGATACAGATTAAATCAGA | |
| | ACGCAGAAGCGGTCTGATAAAACAGAATTTGCCTGGCGGC | |
| | AGTAGCGCGGTGGTCCCACCTGACCCCATGCCGAACTCAG | |
| | AAGTGAAACGCCGTAGCGCCGATGGTAGTGTGGGGTCTCC | |
| | CCATGCGAGAGTAGGGAACTGCCAGGCATCAAATAAAACG | |
| | AAAGGCTCAGTCGAAAGACTGGGCCTTTCGTTTTATCTGTT | |
| | GTTTGTCGGTGAACGCTCTCCTGAGTAGGACAAATCCGCCG | |
| | GGAGCGGATTTGAACGTTGCGAAGCAACGGCCCGGAGGG | |
| | TGGCGGGCAGGACGCCCGCCATAAACTGCCAGGCATCAAA | |
| | TTAAGCAGAAGGCCATCCTGACGGATGGCCTTTTTGCGTTT | |
| | CTACAAACTCTCTCGAGCACCACCACCACCACCACTGAGAT | |
| | CCGGCTGCTAACAAAGCCCGAAAGGAAGCTGAGTTGGCTG | |
| | CTGCCACCGCTGAGCAATAACTAGCATAACCCCTTGGGGCC | |
| | TCTAAACGGGTCTTGAGGGGTTTTTTGCTGAAAGGAGGAA | |
| | CTATATCCGGAT | |

Seq. ID 2 encodes for 33 amino acid carrier peptide, truncated yebf peptide, represented by Seq. ID 4, and Seq. ID 3 encodes for peptide represented by Seq. 5. The Seq. ID 3 is synthesized by mutating Seq. ID 2, wherein, TGC codon at position 40 in Seq. ID 2 is mutated to GCG codon, to mutate Cys at position 14 of Seq. ID 4 to Ala at position 14 of Seq. ID 5.

In another embodiment, the invention provides Seq. ID 6 representing the DNA sequence of expression vector comprising Seq. ID 1 encoding recombinant GLP-1 peptide, in conjugation with secretory signal sequence comprising of combination of signal peptide of the gene ompf and the DNA sequence carrier peptide of Seq. ID 3 encoding truncated yebf peptide of Seq. ID 5.

In yet another embodiment, as described in Table 2, the invention provides a chemically defined media for growing and culturing bacteria transformed with the bacterial expression vector with DNA sequence encoding recombinant GLP-1 peptide, wherein, the media is devoid of any complex undefined materials which tend to decrease the solubility of secreted recombinant proteins in the culture media and reduce the final amount of recombinant proteins purified. The media comprises of at least one carbon source, more specifically, glucose/dextrose; and glycerol as a stabilizing agent, wherein the ratio of glucose/dextrose and glycerol is between 1:0.25 to 1:1, preferably, 1:0.5. Presence of glycerol in media is to prevent the high shearing forces and protect bacteria from damage, and to reduce denaturation of recombinant protein. The media further comprises of at least one nitrogen source, wherein the nitrogen source is an ammonium salt. Further, the media comprises of citric acid in the range of 5 to 25 mM. Citric acid's function in the said chemically defined media is to prevent infection of *E. coli* with bacteriophage. Infection of *E. coli* with bacteriophages is common problem in bacterial cultures which leads to decrease in number of live bacterial cells in the culture, this inversely affects the production of recombinant protein thereby reducing its production. Mechanistically, bacteriophages are very sensitive to citric acid and unable to infect the bacteria in the presence of citric acid. The common LB broth used for recombinant protein production lacks citric acid and is not effective in preventing bacteriophage infection in *E. coli*. The media also comprises of salts of magnesium, potassium, phosphorus, and sodium; and salts of trace elements selected from the group to not limited to iron, cobalt, manganese, copper, boron, molybdenum, and zinc. Additionally, the media also comprises of glycine which plays an important role in maintenance of membrane potential of bacterial cells and enhances protein secretion; and arginine which acts a chaperone molecule and enhances recombinant protein folding intracellularly, thereby reducing formation of inclusion bodies or aggregates and facilitates secretion of folded recombinant proteins extracellularly. Glycine enhances the secretion, whereas Arginine aids in folding of protein before secretion. Together, Glycine and Arginine, help secretion of recombinant proteins. Additionally, the media comprises of at least one chelating agent including but not limited to Ethylenediaminetetraacetic acid (EDTA), and at least one vitamin, more specifically, thiamine.

TABLE 2

Composition of chemically defined starter culture media, initial batch media, and perfusion media.

| Main Components of the media | Concentration range (mM) |
|---|---|
| Citric Acid | 5 to 25 mM |
| KH2PO4 | 50 to 150 mM |
| (NH4)2HPO4 | 10 to 50 mM |
| NACL | 1 to 10 mM |
| GLYCINE | 1 to 10 mM |
| GLYCEROL | 10-100 mM |
| ARGININE | 0.5 to 10 mM |
| CACL2 | 0.01 to 1 mM |
| MGSO4•7H2O | 1 to 10 mM |
| DEXTROSE | 20 to 200 mM |
| KANAMYCIN | 20 to 200 mM |
| THIAMINE | 0.001 to 1 mM |

| Salts of Trace elements in media | Gram per Litre |
|---|---|
| Fe(III) citrate | 1 to 5 g |
| CoCl2-6H2O | 0.1 to 2 g |
| MnCl2-4H2O | 0.5 to 5 g |
| CuCl2-2H2O | 0.01 to 1 g |

TABLE 2-continued

Composition of chemically defined starter culture media, initial batch media, and perfusion media.

| | |
|---|---|
| H3BO3 | 0.1 to 1 g |
| Na2MoO4-2H2O | 0.01 to 1 g |
| Zn acetate-2H2O | 0.5 to 5 g |
| EDTA | 0.01 to 5 g |

In another embodiment, the invention provides a method for producing and secreting recombinant GLP-1 by *E. coli*, using a perfusion-based fermentation system for continuous production and separation of secreted recombinant GLP-1 peptide. The method comprises the steps of:

a) transforming *E. coli* with an expression vector encoding recombinant GLP-1 peptide, to produce recombinant *E. coli*;

b) preparing a starter culture of recombinant *E. coli* by growing the culture at 37° C. with 225 rpm for 12 hours in a starter culture growth media till $OD_{600}$ of the starter culture reaches 5.0-6.0;

c) preparing a perfusion-based fermenter system by adding initial batch media to the fermenter vessel comprising of glucose/dextrose at a concentration of 10 g/L and maintaining the pH at 6.9;

d) adding the starter culture to the fermenter vessel and maintaining the pH at 6.9 using 3N NaOH in the first hour and after first hour using 4M liquid ammonia for maintaining pH at 6.9;

e) adding lac operon inducing agent such as lactose or lactose analogs to the fermenter vessel when the residual glucose/dextrose concentration in the initial batch media has reduced to ~5 g/L for induction of production and secretion of recombinant GLP-1 peptide from recombinant *E. coli*; and f) initiating perfusion-based fermentation system after 30-40 mins of induction for separating the recombinant *E. coli* as retentate from the spent culture media containing the secreted recombinant GLP-1 peptide as permeate, harvesting recombinant GLP-1 peptide from the permeate, and re-feeding the fermenter vessel with fresh perfusion media and with the retentate recombinant *E. coli* for continuous production and secretion of recombinant GLP-1 peptide.

The perfusion system involves growing the recombinant *E. coli* in perfusion suspension culture, wherein the culture medium including the bacteria is circulated over a separation system in alternating tangential flow, and the separation system removes a filtrate containing spent medium containing recombinant GLP-1 peptide from the culture medium and retains the bacteria in the culture medium for continuous production.

Figure 2:
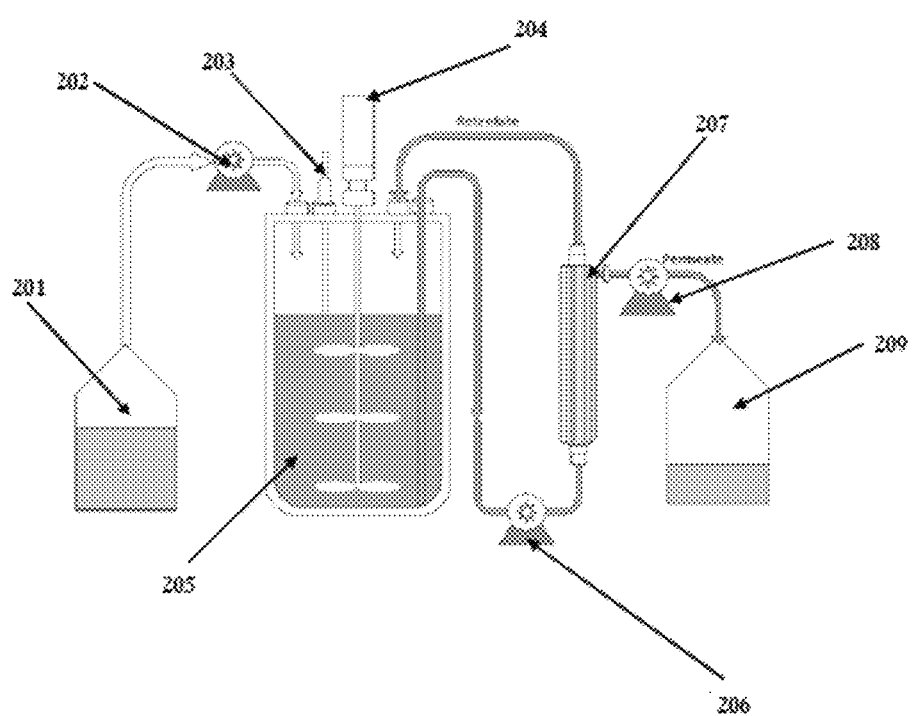

FIG. 2 elucidates the schematic diagram of perfusion-based fermentation and separation system, the system comprising a feed tank (201); a feed pump (202); a level sensor (203); a motor (204); a fermenter vessel (205); a magnetic levitation pump (206); separation module (207); harvest pump (208), and a harvest tank (209), wherein hollow fiber column in the separation module (207) comprises a filter module of hollow fiber membranes suitable for the removal of secreted recombinant GLP-1 peptide from the culture medium.

The feed tank (201) stores media that are pumped via a feed pump (202) to a fermenter vessel (205). The fermenter vessel (205) holding the culturing suspension comprising of *E. coli* starter culture and the media is agitated by a motor (204). The fermenter vessel (205) is continuously or intermittently drained via a magnetic levitation pump (206). The level of media is maintained via a level sensor (203). The drained liquid is further passed through a filter module comprising hollow fiber membranes. The culturing suspension in the fermenter vessel (205) is circulated over a separation system in alternating tangential filtration flow. The separation module (207) separates recombinant *E. coli* as retentate, and the spent culture media comprising the recombinant GLP-1 peptide as permeate. The suspension filtered via a filter module further comprising hollow fiber membranes suitably removes the recombinant GLP-1 from the spent culture medium. The filtered *E. coli* in the retentate is re-introduced into the fermenter vessel. The spent culture media is pumped via a harvest pump (208) to the harvest tank (209).

In an embodiment of the preferred invention the separation system comprises a filter module comprising hollow fibers, e.g. hollow fibers made of polysulphone, Methyl Ester or Cellulose ester having a porosity of between 0.4 μm and 0.1 μm, e.g. a porosity of 0.2 μm for the removal of secreted recombinant GLP-1 peptide from the spent culture medium.

In yet another embodiment, the separation system comprises a filter module comprising membranes wherein the membranes have a molecular weight cut-off pore size of 500 kDa.

Example 1

*E. coli* Culture and Transformation

Seq. ID 6 representing the DNA sequence of expression vector comprising Seq. ID 1 encoding recombinant GLP-1 peptide in conjugation with secretory signal sequence having the combination of signal peptide of the gene ompf and the DNA sequence carrier peptide of Seq. ID 3 encoding truncated yebf peptide of Seq. ID was used for all experimental procedures.

*E. coli* BL21(DE3) strain was chosen as expression system and it is transformed by chemical transformation method (i.e. CaCl2)) by taking 100 ng of recombinant vector Seq. ID 6. Chemical competent cells (i.e B21(DE3)) were incubated at 4° C. after taken out from −80° C. freezer and allowed to thaw. After thawing cell to 4° C., vector was added and incubated for 15 minutes at same 4° C. Thereafter incubation heat shock was applied to cells by exposing them to 42° C. for about 1 minute. After application of heat shock, transformed *E. coli* cells were kept at 4° C. for about 15 minutes. There upon cells were grown by addition of Luria broth (LB) media for 40 minutes. Later grown cells were spread on LB agar with appropriate antibiotic selection criteria.

Example 2

Batch Fermentation and Perfusion-Based Fermentation a) Preparation of Starter Culture Adequate amount of pre-culture was prepared to carryout fed-batch fermentation using autoclaved starter culture media of composition described in Table 3. Typically, 300 ml of growth media is taken in 2 litre flask and inoculated with single colony forming unit aseptically from transformed plate and incubated in rotatory incubator maintained at 37° C. with 225 rpm for 12 hours. Filter sterilized media components such as Thiamine, Trace elements are reconstituted while setting up starter culture. End of 12 hours of incubation $OD_{600}$ reaches ~5.0.

b) Batch-Fermentation Process

Bioreactor with growth media of composition of initial batch media described in Table 3 is autoclaved at 121° C. with holding time of 45 minutes and later whole assembled bioreactor is brought down to 37° C. by help of control tower having SCADA software. During bioreactor packing all the requirement dosing tubing 0.2 micron hydrophobic filter for air inlet and exhaust unit, Dissolved Oxygen probe, pH probe, baffle, impeller blades kept at 1:1 L/D ratio are attached.

Fermentation process is started by maintaining required physical condition such as pH at 6.90, temperature at 37° C. Based on growth profile variable parameters such as aeration, agitation is automatically controlled by Control Unit. Aseptically starter culture is transferred to bioreactor. Reconstitution of filter sterilized media components such as thiamine, trace elements are aseptically given to bioreactor from injection port. During start of fermentation Dextrose is added to make up to the final concentration of 10 g/L. MgSo4 stock solution is given in supplemental form to avoid media precipitation. pH is maintained with the help of 3N NaOH for first hour later 4N Ammonia till end of fermentation process. Cells are grown at maximum growth rate of ~0.6/hr.

Hourly sample are drawn from bioreactor aseptically and cell density is measured using Spectrophotometer set at 600 nm against blank media. Residual glucose is measured using digital glucometer with same sample. After 3 hours of fermentation feeding is done in exponential form. After attaining $OD_{600}$ of ~40 culture is induced with IPTG i.e ~0.25 mM, by making sure that residual glucose is about 5 g/L.

Post induction pH is maintained at 6.90 only with 4N Ammonia. No acid is used throughout the fermentation process. Supplements are added to culture that includes Glycine, Arginine, Glutamic acid to make it to final concentration of 2 mM each. Hourly sample are drawn and centrifuged to separate cells and media and later analyzed using PAGE to detect presence of recombinant protein expression in cells and amount of secretion in media. After end of 6 hour of induction culture is drawn and centrifuged to separate cells and media.

c) Perfusion-Based Fermentation Protocol

Transformed cells are prepared using BL21(DE3) taking appropriate plasmid by giving heat shock and spreading them on selective antibiotic LB agar plate followed by incubation for 12 hour in incubator at 37° C. Growth media is prepared by taking media components and dissolving in deionized water and adjusted to pH 6.90 using 5N NaOH. Starter culture media is sterilized at 121° C. with 45 minutes holding time in autoclave. All the other media component that are heat liable are filter sterilized i.e Thiamine, Kanamycin, Trace elements. Dextrose and $MgSO_4.7H_2O$ are separately autoclaved. Starter culture is prepared by inoculation of colony from LB agar plate into shake flask. Filter sterilized media components i.e Thiamine, Kanamycin 50 mg/Lit, Trace elements 1000× were added along with 1% Dextrose, $MgSO_4.7H_2O$-5 mM, yeast extract 0.2%. Incubated the flask in shaker incubator at 37° C. at 225 rpm for overnight.

Bioreactor vessel packed with pre-calibrated pH probe, antifoam sensor along with new membrane fitted to dissolved oxygen (DO) probe after refilling with Oxylyte, sparger pipe and exhaust pipe fitted with 0.24 hydrophobic vent filter each, baffle. Initial batch media as described in Table 3 is poured into fermenter vessel excluding volume corresponding to reconstitutable media components. Fermenter vessel is autoclaved at 121° C., 45 min holding time, 15 psi, later cooled to room temperature and attached to Control unit. Fermenter vessel is purged with 0.1 standard litre per minute (SLPM) of air overnight for DO probe polarization. DO is calibrated just before addition of starter culture. Reconstitution of media is done before addition of starter culture. Dosing bottles are attached and tubing's are primed. All the parameters are set in Control unit i.e pH set to 6.90 with 0.1% Dead band, DO set to 30% in cascade mode, Acid/Base in auto mode, antifoam sensor with 0.1% Sigma Antifoam 204, Temperature set to 37° C. DO is controlled in cascade mode with Agitation, Gas flow per minute, % of pure oxygen purging. Initial RPM is set to 200. Pre-culture is aseptically transferred into bioreactor. First hour pH is maintained by attaching dosing bottle with 3N NaOH Rest of the batch pH is maintained by 4M Liquid Ammonia. $MgSO_4.7H_2O$ is reconstituted aseptically for three doses from zeroth hour of fermentation. Hourly sampling is done to check cell density by UV/Vis Spectrophotometer and residual glucose by glucometer. After 5 hours or batch with residual glucose of ~5 g/L is picked as ideal time point to induce the culture with 0.2 mM IPTG. Sterile 500 kDa Hollow fiber is connected to perfusion equipment and equilibrated with sterile initial batch media, later tubings are connected to bioreactor. 30 minutes after post induction perfusion is started, here culture is drawn out of vessel automatically by pump passed through hollow fiber, retentate from the hollow fiber which contains the recombinant $E. coli$ cells is sent back to bioreactor. Harvest is collected from permeate end of hollow fiber by setting pump speed to ~16.6 ml/minutes and simultaneously at same flow rate perfusion media is added into fermenter vessel. Total fermentation is run till the completion of perfusion media. After completion of feeding perfusion media, culture is concentrated to $\frac{2}{3}^{rd}$ of batch volume by drawing $\frac{1}{3}^{rd}$ of permeate and batch is terminated. Post induction hourly samples are drawn to check expression and secretion of recombinant GLP-1 peptide. Hollow fibre is sanitized by 0.5N NaOH and stored in 0.1N NaOH.

TABLE 3

Composition of media

| SL. NO | Components | Initial Batch Media Molarity (mM) | Perfusion Media Molarity (mM) |
|---|---|---|---|
| 1 | Citric Acid | 8.84 | 8.84 |
| 2 | KH2PO4 | 97.73 | 97.73 |
| 3 | (NH4)2HPO4 | 30.2 | 30.2 |
| 4 | NACL | 2.13 | 2.13 |
| 5 | GLYCINE | 1 | 1 |
| 6 | GLYCEROL | 54.29 | 54.29 |
| 7 | ARGININE | 1 | 1 |
| 8 | CACL2 | 0.09 | 0.09 |
| 9 | MGSO4•7H20 | 5 | 1 |
| 10 | DEXTROSE | 139 | 13.9 |
| 11 | KANAMYCIN | 0.05 | 0.05 |
| 12 | THIAMINE | 0.06 | 0.06 |
| 13 | IPTG | 0 | 0.2 |

Example 3

Efficiency of Growth of Recombinant Bacteria and Secretion of Recombinant Glp-1 Peptide Growth kinetics, glucose consumption, and recombinant protein production and secretion in the culture media was tested at different times using batch fermentation process.

Figure 3A:
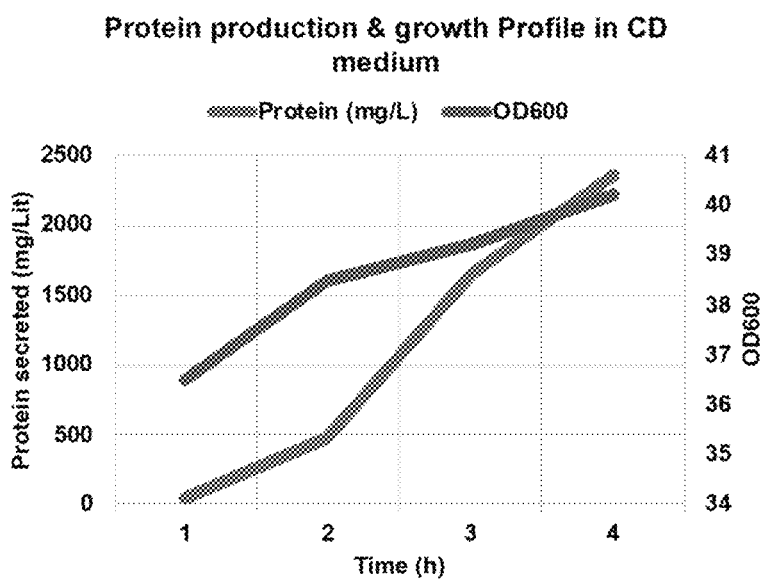
FIG. 3a is a graphical representation of growth kinetics of recombinant E. coli transformed with expression vector Seq. ID 6 and recombinant GLP-1 peptide secretion over time in batch fermentation process.

FIG. 3a provides a line graph representing the production of recombinant GLP-1 peptide of 10 kDa in conjugation with secretory signal sequence and affinity tag and growth of recombinant $E. coli$ at indicated time points, which suggests steady growth of bacteria and increase in recombinant protein secretion in media. However, under batch method, less than 2.5 g/L is produced at the completion of the batch fermentation process at 4 hours.

Figure 3B:
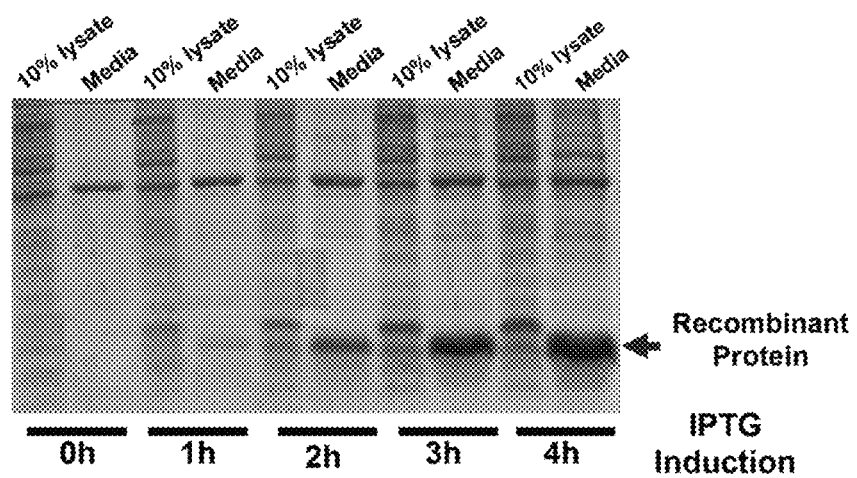
FIG. 3b is representative image of SDS-PAGE comparing recombinant E. coli transformed with expression vector Seq. ID 6 cell lysates and culture media to detect recombinant GLP-1 peptide after different time points of 0.25 mM IPTG induction.

Further, five microliters of culture supernatant were collected during fermentation at indicated time points after induction using IPTG, and recombinant $E. coli$ cell lysates from respective time points were also collected and then analyzed by reduced SDS-PAGE and compared. As depicted in FIG. 3b, within 1 hour of induction the recombinant GLP-1 peptide started to be produced and secreted by the bacteria. This steadily increased with time. Moreover, there was hardly any recombinant GLP-1 peptide present in cell lysates suggesting efficient secretion by the recombinant bacteria. This suggested the efficiency of the vector Seq. ID 6 in secretion of the recombinant GLP-1 peptide enabled by the chemically defined batch media composition.

Figure 4:
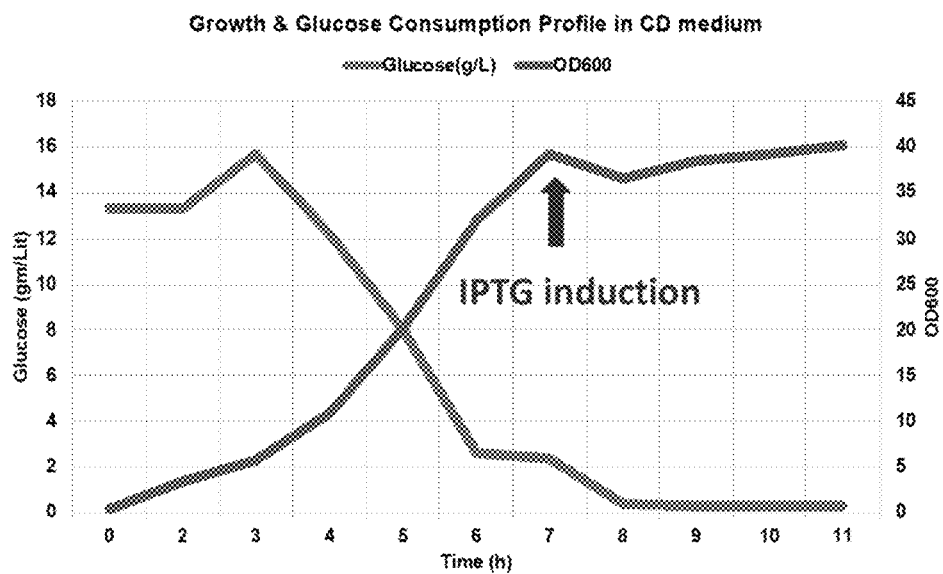
FIG. 4 is a graphical representation of growth kinetics of recombinant E. coli transformed with expression vector Seq. ID 6 and glucose consumption over time in batch fermentation process.

The glucose consumption during the fermentation process was also analyzed. As depicted in FIG. 4, glucose consumption starts at optimal rate soon after 1 hour of inoculation of starter culture to the perfusion-based fermentation process. We standardized and established adequate amount of glucose that need to be added prior to start of the cell proliferation stage to achieve maximal growth rate thereby adequate cell density is attained soon. Yield from per gram glucose remains optimal with thereby making the method economical and reliable compared to traditional cell proliferation techniques. Initial batch media has 10 g/L concentration of glucose/dextrose, and induction is carried out when the residual glucose/dextrose concentration reaches around 5 g/L. Hence the use of the vector of Seq. ID 6 along with the chemically defined batch media is optimal for growth and secretion of the recombinant GLP-1 peptide.

Example 4

Enterokinase Digestion of Recombinant Glp-1 Peptide

The DNA sequence encoding recombinant GLP-1 peptide is separated from the secretory signal sequence by Enterokinase recognition sequence (DDDDK) to enable separation of recombinant GLP-1 peptide from the secretory signal sequence after harvesting the recombinant GLP-1 peptide. The GLP-1 peptide is in tandem with His-tag for purification process.

As depicted in FIG. 5, the recombinant GLP-1 peptide is secreted in the media and after purification using His-affinity chromatography once digested with enterokinase produces smaller bands suggesting separation of secretory signal sequence.

Example 5

Recombinant Glp-1 Peptide Production by Perfusion-Based Fermentation

The perfusion-based fermentation process was carried out using recombinant $E. coli$ transformed with Seq. ID 6 as explained example 2c. At any time point the fermenter can hold 1 litre of media for fermentation which is filtered for recovering recombinant bacteria and spent media containing secreted recombinant GLP-1 peptide. Secreted recombinant protein is continuously harvested at a rate of 1 L/hour by removing spent media. Once the spent media is removed, the fermenter is re-fed with equal amount of fresh perfusion media and retentate E. coli for continuous fermentation and so on. Every hour a small amount of sample is collected for quantification and analysis. In one continuous batch of perfusion fermentation a total of 10 L of media is fermented for a period of 10 hours.

FIG. 6a elucidates the growth curve of the bacterial cells fermented in the perfusion-based fermentation system. After 5 hours or batch with residual glucose of ~5 g/L, induction using IPTG was started. After $1^{st}$ hour of induction, perfusion was started to supplement limiting nutrients in order to keep the cell proliferation at minimal rate. As depicted in FIG. 6a, the E. coli $OD_{600}$ is maintained between 8-10. Also most the time is dedicated for recombinant protein production instead of increase in bacteria number.

Media samples were collected and analysed after 0, 2, 4 and 6 hours of induction with 0.25 mM IPTG in perfusion method where a total of 9 Litres of media containing recombinant protein was collected for SDS-PAGE analysis. As depicted in FIG. 6b, 10 kDa recombinant GLP-1 peptide secretion is seen after induction with IPTG as soon as 2 hours and the amount of recombinant GLP-1 peptide secreted is almost same even after 6 hours. This clearly indicates that continuous production of recombinant GLP-1 peptide is seen perfusion-based fermentation method consistently over a long period of time.

As depicted in FIG. 6c, within $1^{st}$ hour itself the production of the recombinant GLP-1 peptide reach 1 g/L and even after $10^{th}$ hour the production rate was around 1 g/L. This suggested steady production of recombinant GLP-1 peptide at a rate of 1 g/L/hr using Seq. ID 6 with chemically defined media using perfusion-based fermentation method.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention.

We claim:

1. A method for continuous production and secretion of recombinant GLP-1 peptide by *E. coli*, comprising the steps of:

a) transforming *E. coli* with an expression vector encoding recombinant GLP-1 peptide to produce recombinant *E. coli*;

b) preparing a starter culture of recombinant *E. coli* by growing the culture at 37° C. with 225 rpm for 12 hours in a starter culture growth media until the $OD_{600}$ of the starter culture reaches 5.0-6.0;

c) preparing a perfusion-based fermenter system by adding initial batch media to the fermenter vessel comprising of glucose/dextrose at a concentration of 10 g/L and maintaining the pH at 6.9;

d) adding the starter culture to the fermenter vessel and maintaining the pH at 6.9;

e) adding lac operon inducing to the fermenter vessel when the residual glucose/dextrose concentration in the initial batch media has reduced to ~5 g/L for the induction of production and secretion of recombinant GLP-1 peptide from recombinant *E. coli*; and f) initiating perfusion-based fermentation system after 30-40 mins of induction for separating the recombinant *E. coli* as retentate from the spent culture media containing the secreted recombinant GLP-1 peptide as permeate, harvesting recombinant GLP-1 peptide from the permeate, and re-feeding the fermenter vessel with fresh perfusion media and with the retentate recombinant *E. coli* for continuous production and secretion of recombinant GLP-1 peptide;

wherein, the expression vector consists of SEQ ID NO: 6, wherein, said expression vector includes: the DNA sequence consisting of SEQ ID NO: 1 which encodes the recombinant GLP-1 peptide, the DNA sequence consisting of SEQ ID NO: 3 which encodes the secretory signal peptide of the gene ompf, and a DNA sequence encoding a truncated YebF peptide of SEQ ID NO:5;

wherein, the expression vector, encoding recombinant GLP-1 peptide, of SEQ ID NO: 6 secretes recombinant GLP-1 peptide in the range of 1-1.2 g/L/hr by a perfusion-based fermentation system;

wherein, the initial batch media is a chemically defined media comprising of: 139 mM glucose/dextrose; 30.2 mM diammonium phosphate; 54.29 mM glycerol as stabilizing agent; 8.84 mM citric acid; 1 mM glycine as essential amino acid; 1 mM arginine as positively charged amino acid; 0.06 mM thiamine; 5 mM magnesium sulfate heptahydrate; 97.73 mM potassium dihydrogenphosphate; 2.13 mM sodium chloride; 0.09 mM calcium chloride; and salts of trace elements Fe (III) citrate at 1-5g/L, $CoCl_2$-$6H_2O$ at 0.1-2 g/L, $MnCl_2$-$4H_2O$ at 0.5-5 g/L, $CuCl_2$-$2H_2O$ 0.01-1 g/L, $H_3BO_3$ at 0.1-1 g/L, $Na_2MoO_4$-$2H_2O$ at 0.01-1 g/L, Zn acetate-$2H_2O$ at 0.5-5 g/L concentrations; and chelating agent EDTA at 0.01-5 g/L concentration;

and wherein, the perfusion media is a chemically defined media comprising of 13.9 mM glucose/dextrose; 30.2 mM diammonium phosphate; 54.29 mM glycerol as stabilizing agent; 8.84 mM citric acid; 1 mM glycine as essential amino acid; 1 mM arginine as positively charged amino acid; 0.06 mM thiamine; 5 mM magnesium sulfate heptahydrate; 97.73 mM potassium dihydrogenphosphate; 2.13 mM sodium chloride; 0.09 mM calcium chloride; and salts of trace elements Fe (III) citrate at 1-5 g/L, $CoCl_2$-$6H_2O$ at 0.1-2 g/L, $MnCl_2$-$4H_2O$ at 0.5-5 g/L, $CuCl_2$-$2H_2O$ 0.01-1 g/L, $H_3BO_3$ at 0.1-1 g/L, $Na_2MoO_4$-$2H_2O$ at 0.01-1 g/L, Zn acetate-$2H_2O$ at 0.5-5 g/L concentrations; and chelating agent EDTA at 0.01-5 g/L concentration.

2. The method as claimed in claim 1, wherein, the perfusion-based fermentation system comprises a feed tank (201); a feed pump (202); a level sensor (203); a motor (204); a fermenter vessel (205); a magnetic levitation pump (206); separation module (207); harvest pump (208), and a harvest tank (209), wherein, the separation module (207) comprises a filter module of hollow fiber membranes suitable for the removal of secreted recombinant protein from the culture medium; and the filter module of hollow fiber membranes comprises of polysulphone and methyl ester or cellulose ester having a porosity of 0.2 μm; and the membranes have a cut-off pore size of 500 kDa.

3. The method as claimed in claim 1, wherein, the perfusion-based fermentation system enables culture medium including the recombinant *E. coli* to be circulated over a separation system in alternating tangential flow, and the separation system removes a filtrate containing spent medium containing recombinant GLP-1 peptide from the culture medium and retains the recombinant *E. coli* in the culture medium for continuous production.

* * * * *